United States Patent [19]
Ghodsian

[11] Patent Number: 5,755,680
[45] Date of Patent: May 26, 1998

[54] METHOD FOR INHIBITING THE FORMATION OF STRIATIONS DUE TO SKIN TENSION

[76] Inventor: Kamran Ghodsian, 32 Hillsdale Dr., Newport Beach, Calif. 92660

[21] Appl. No.: 821,402

[22] Filed: Mar. 20, 1997

Related U.S. Application Data

[63] Continuation-in-part of Ser. No. 590,592, Jan. 24, 1996, abandoned, which is a continuation-in-part of Ser. No. 332,925, Nov. 1, 1994, abandoned.

[51] Int. Cl.⁶ .................................................. A61F 5/00
[52] U.S. Cl. .............................. 602/52; 602/54; 602/57; 602/58
[58] Field of Search .................... 602/41–59, 60; 606/204.35

[56] References Cited

U.S. PATENT DOCUMENTS

| | | | |
|---|---|---|---|
| 2,392,377 | 1/1946 | Golding | 606/204.35 |
| 3,949,072 | 4/1976 | Tenta | 424/145 |
| 4,054,649 | 10/1977 | Cariel | 424/195 |
| 4,112,121 | 9/1978 | Tenta | 424/346 |
| 4,871,752 | 10/1989 | Ilg et al. | 514/355 |
| 5,134,163 | 7/1992 | Kligman | 514/559 |
| 5,153,174 | 10/1992 | Band et al. | 514/12 |
| 5,176,919 | 1/1993 | Bertini Curri et al. | 424/450 |
| 5,444,091 | 8/1995 | Rapaport et al. | 514/557 |
| 5,468,495 | 11/1995 | Kligman | 424/401 |
| 5,472,713 | 12/1995 | Fein et al. | 424/522 |
| 5,538,740 | 7/1996 | Abad | 424/547 |

*Primary Examiner*—Richard J. Apley
*Assistant Examiner*—Kim M. Lee
*Attorney, Agent, or Firm*—Harold L. Jackson

[57] ABSTRACT

A method of inhibiting the stretching of the skin to prevent damage to the skin, and resulting stretch marks (striations) on a woman's abdominal area during pregnancy, by transversely taping an adhesive-backed polyurethane sheet over the affected area for a major portion of the pregnancy period.

10 Claims, 1 Drawing Sheet

METHOD FOR INHIBITING THE FORMATION OF STRIATIONS DUE TO SKIN TENSION

RELATED APPLICATIONS

This application is a continuation-in-part of my application Ser. No. 08/590,592 filed Jan. 24, 1996, now abandoned, entitled A METHOD FOR INHIBITING THE FORMATION OF STRIATIONS DUE TO SKIN TENSION which, in turn, is a continuation-in-part of my application Ser. No. 332,925 filed Nov. 1, 1994 now abandoned, entitled MEANS TO PREVENT STRIATION DUE TO SKIN TENSION.

BACKGROUND OF THE INVENTION

FIELD OF THE INVENTION

The present invention relates to a method for inhibiting or preventing the formation of striations on the surface of the skin. Such striations, often referred to as stretch marks, are common results of pregnancy.

Human skin has two distinct layers. The first or outer layer consists of epithelial cells (also existing in a layered configuration) attached to each other and forming the surface of the skin. The outer layer is often referred to as the epidermis. The second or inner layer is a connective underlying tissue. This underlying tissue is attached to the epidermis and includes a network of elastic fibers which extend between bundles of collagen (dermis). The elastic fibers have rubber like properties, that is, they stretch easily and return to their original length when the deforming force is removed. The direction of all fibers is parallel to the surface. Other elements of the dermis are fibroblastic, macrophage, fat cells.

For some reason, which to my knowledge is not yet completely understood, the elastic fibers and colagens of the dermis (intradermal connective tissue) are very frequently dissolved or weakened due to hormonal changes during pregnancy. The striations may be a result of excess in adrenocortical hormones.

The mechanism by which corticosteroid induce striae is believed to be due to the inhibition of collagen fiber formation.

In the early stage, light microscopic findings are subtle. The connective tissue is separated by edema and there is mild chronic inflammation. Late in the disease, the epidermis and dermis are thinned. The individual collagen fibers are thin, layered and oriented in the direction of the stress. Elastic fibers are decreased in number or absent and may appear frayed.

Electron microscope studies demonstrate thin elastic tissue fibers in early striae. During the late stage, the fibers appear thickened.

The change in the intradermal connective tissue is not generalized but is segmental. As a result the elastic fibers of the healthy areas will place the weak fibers of the weakened areas in traction and pull the epidermis in the weakened areas toward the healthy areas. The net result is that the epidermis or outer skin layer in the weakened areas will stretch and provide unsightly striations of the skin.

There is a need to inhibit stretching of the epidermis which would otherwise occur when the underlying elastic fibers are degraded due to pregnancy.

SUMMARY OF THE INVENTION

One of the objects of the present invention is to describe a method for preventing skin striations to occur because of skin tension resulting from pregnancy or other hormonal changes.

In accordance with my invention I provide a adhesive-backed flexible reinforcing membrane which will form a bridge between the healthy and the weakened or otherwise impaired areas to prevent the tensile forces between these healthy areas from stretching the epidermis of the impaired areas. By placing such a membrane over the surface of the skin to bridge the healthy areas of the dermis, the whole epidermis area is reinforced and stabilized. The membrane effectively neutralizes the forces of the elastic and collagen fibers of the heathy dermis areas and prevents the impaired areas from being stretched out causing stretch marks to appear. Once the cause is treated by delivery to allow the elastic fibers of the impaired areas to repair their strength, the stretch-preventing membrane can be removed.

It is therefore an object of the invention to provide a very thin sheet of suitable plastic material in the form of a breathable polyurethane or copolyester film covered with an adhesive backing which may be secured to the affected areas of the body to prevent the separation of the epidermis by reinforcing the surface during the time that the body is undergoing the hormonal changes.

It may thus be seen that the objects of the present invention set forth herein, as well as those made apparent from the following description, are efficiently attained. While the preferred embodiment of the invention has been set forth for purposes of disclosure, modifications of the disclosed embodiments of the invention as well as other embodiments thereof may occur to those skilled in the art. Accordingly, the appended claims are intended to cover all embodiments which do not depart from the spirit and scope of the invention.

BRIEF DESCRIPTION OF THE DRAWINGS

Novel features and advantages of the present invention in addition to those mentioned above will become apparent to those skilled in the art from reading the following detailed description in conjunction with the accompanying drawings wherein.

DESCRIPTION OF THE PREFERRED EMBODIMENT

Figure 1:
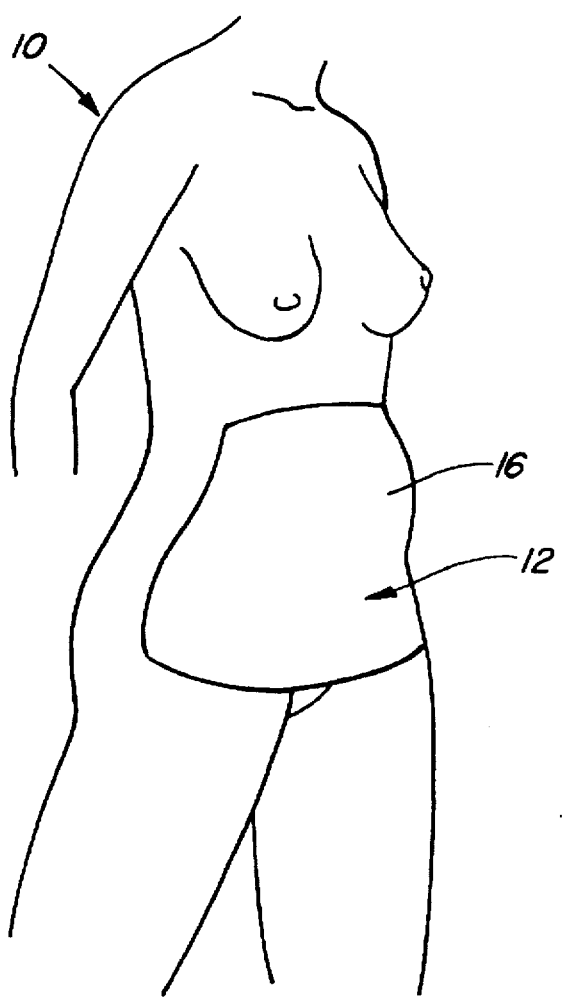
FIG. 1 is a pictorial view of a pregnant woman on whom is positioned and taped a one-piece sheet of material in accordance with the present invention (e.g., adhesive backed membrane) that is adhesively secured about the abdominal area and a second sheet positioned and taped about the breast area.
Figure 2:
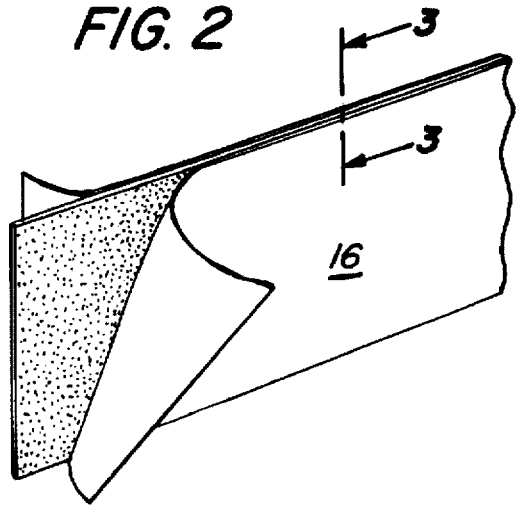
FIG. 2 is an enlarged end view of a small portion of the sheet as shown in FIG. 1.
Figure 3:
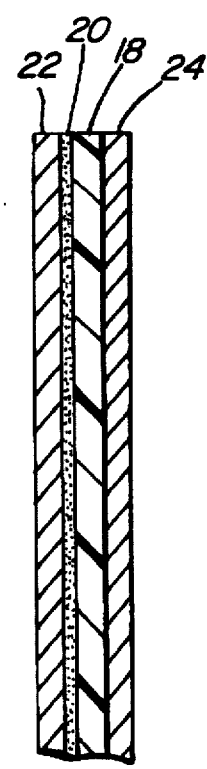
FIG. 3 is a cross-sectional view of the sheet of FIGS. 1 and 2.

Referring now to FIGS. 1–3, there is illustrated a body, generally indicate at 10, of a female having a enlarged abdominal area 12 which is due to a pregnancy condition. In accordance with the present invention, the area is covered by stretch preventing membrane 16 adapted to prevent stretching of the individual's underlying skin. The stretch prevention membrane 16 comprises a thin adhesive-backed-high-moisture-vaporization-elastomer film 18. Such a film may be made from polyurethane, a copolyester, or a block copolymer. The film 18 preferably has a thickness not exceeding 0.0020 inches (e.g., 2.0 mil.) and most preferably has a thickness within the range of about 0.5 to 1.0 mil. The adhesive 20 is applied to one surface of the film within the range of about 0.5 to 0.1 mil. in thickness.

The adhesive is also preferably pressure-sensitive and nonsensitizing hypoallergenic. The adhesive may be an acrylic copolymer. The adhesive properties may have a typical peel adhesion value within the range of about 300 to 900 g/in.$^2$, and preferably within the range of about 400 to 600 g/cm$^2$.

The moisture-vapor-transmission rate of the adhesive-backed film or membrane is preferably within the range of about 1,000 to 12,000 g/m$^2$/day.

A releasable backing sheet 22, made of silicon-coated paper, for example, may be placed over the adhesive coating and subsequently removed when the membrane is to be applied to a patient's or individual's skin. Another releasable backing sheet 24 may be placed over the film 18, if desired, as is shown in FIG. 3.

The adhesive backed film or sheet 16 preferably has a ratio of tensile strength in pounds/inch width (lbs/in. width) to elongation in inches within the range of about 1.0 to 2.0 with applied loads of 3 to 7 lbs/in. width and most preferably about 1.25 to 1.50. For example, with an applied load of about 5 lbs/in. width, the elongation of an adhesive-backed polyurethane film is preferably about 350% and at 3.0 lbs/in. width the elongation is about 275%.

The presence of the stretch preventing membrane 16 inhibits and substantially prevents separation of the epidermis tissue during the time that portions of the underlying dermis structure are undergoing adverse changes, that is, losing their elasticity and strength, (due to changes in the elastic fibers and collagen tissue) necessary to hold the epidermis in a cohesive structure and prevent separation of the epidermis or outer skin layer.

The film may be provided with a multiplicity of very small or microscopic holes to enhance its breathability.

Two suitable materials (polyurethane and copolyester, respectively) for use in the present invention are marketed by the Specialty Tape Division of Avery Dennison under the product number MED 5020 and by Bertek, Inc. Under the product name Medifilm 325 (or 390,426). Both films are provided with a pressure sensitive adhesive backing. These films are marketed for securing IV's in place and for covering wounds.

The membrane sheet 16 has a length (extending horizontally about the body) of say about 20 cm or more and a width of at least 10 cm (i.e., 10–20 cm) to accommodate a women's lower and upper abdominal area which expands due to pregnancy. The membrane may be considerably larger than the above dimensions depending upon the size of the individual. Preferably the membrane should cover approximately the area between the symphyses pubis to the xyphoid, in width, and extend lengthwise from 10 to 20 cm on each side of the midline (or the linea nigra) of the abdomen. Such area may be referred to as the major area of the abdomen which is likely to develop stretch marks during pregnancy.

In accordance with my method, the membrane is taped across the surface area of the body when the elastic fibers of the underlying tissue or dermis may be or is being subjected to excessive stress, e.g., during the sixteenth-fortieth week of pregnancy. Talcum power, titanium oxide powder or other suitable non-sensitizing moisture absorbent powder may first be applied to the skin area to receive the membrane. Preferably a non-oily, quick-drying, emulsion-based lotion is applied to the skin area prior to the application of the membrane. The lotion provides moisturizing and emollient properties while the membrane is in place and is very important for the comfortable release of the adhesive when the membrane is removed. In addition, the lotion should provide a correct balance for skin ph, antioxidant and antibacterial properties and stabilize the emulsion. One such lotion is sold under the tradename Nivea. The lotion aids in the subsequent, relatively pain-free, removal of the membrane without adversely affecting the ability of the adhesive-backed film to reinforce and stabilize the underlying epidermis area.

The membrane is to be left in place for an extended period of time until the underlying cause for the degradation of the elastic fibers or dermis has been removed during the term of the pregnancy. For example, the membrane should be left in place about 75 to 90% of the time, and preferably about 80–95% of the time, from about the twentieth week of the pregnancy through the termination of the pregnancy and preferably from about the sixteenth week through the fortieth week, or sooner if the pregnancy is terminated before the fortieth week.

It should be noted that development of stretch marks in the epidermis is a slow process and it is not necessary for the patient or individual to have the stretch prevention sheet to be continuously attached to the area to be protected. While the membrane may be left in place during a shower or bath, it can be removed for short periods of time, if desire, to allow the individual to wash the area underlying the membrane.

Figure 4:
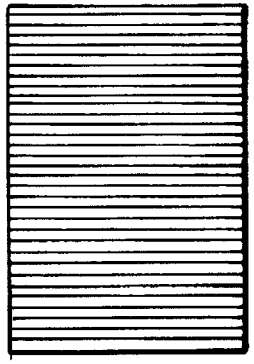
FIG. 4 is a top plan view of an adhesive backed membrane with lateral markings thereon spaced one centimeter apart.

FIG. 4 illustrates a sheet of the adhesive backed membrane with one centimeter markings 26 thereon to aid one in cutting the sheet to the desired length.

The foregoing should only be considered as illustrative of the principles of the invention. Further, since numerous modifications and changes may readily occur to those skilled in the art, it is not desired to limit the invention to the exact construction and operation as shown and described, and accordingly, all suitable modifications and equivalents may be resorted to, falling within the scope of the claimed invention.

What is claimed is:

1. A method of inhibiting the formation of stretch marks on a woman's abdominal area during pregnancy comprising:
   forming a thin adhesive-backed membrane film from the group consisting of polyurethane, copolymer and block copolymer having a sufficient tensile strength to inhibit the elastic fibers in healthy portions of the dermis from excessively stretching the epidermis overlaying unhealthy portions of the dermis while accommodating the expansion of the dermis through cell growth, the membrane having a vapor-transmission rate within the range of 1,500 to 12,200 g/m$^2$/day and a length and width of at least 20 cm and 10 cm, respectively;
   securing the membrane over approximately the major area of the woman's abdomen which is subject to development of striations; and
   maintaining the membrane in place for about 75% to 90% of the time from about the twentieth week of pregnancy through about the termination of the pregnancy.

2. The method of claim 1 wherein the membrane is maintained in place for about 75–90% of the time for about twenty-five weeks commencing with the sixteenth week of pregnancy.

3. The method of claim 2 wherein the forming step comprises providing a member film having a thickness not exceeding 2.0 mil. and coating one side of the film with a pressure-sensitive adhesive which is nonirritating and non-sensitizing to humans, the adhesive backed membrane having a peel adhesion value in the range of about 300 to 900 g/in.

4. The method of claim 3 wherein the forming step includes providing a film having a thickness of about 1 mil. and coating one surface of the film with a acrylic copolymer having peel adhesion value within the range of about 400 to 600 g/in$^2$ and a thickness of about 0.5 to 1.0 mil.

5. The method of claim 4 wherein the forming step includes forming the membrane with a length and width of at least 40 cm and 20 cm. respectively.

6. The method of claim 5 further including the step of applying a nonsensitizing moisture absorbent material to said area prior to the step of securing the membrane.

7. The method of claim 6 wherein said absorbent material comprises a non-oily, quick-drying, emulsion-based lotion which provides moisturizing and emollient properties while the membrane is in place and acts as a releasing agent for the adhesive when the membrane is removed.

8. In a method of substantially preventing the formation of stretch marks on a woman's abdominal area during pregnancy through the use of an adhesive-backed breathable membrane having a moisture vapor transmission rate within the range of 1,500 to 12,000 g/m$^2$/day, a thickness in the range of about 0.5 to 2.0 mil., a length and width of at least 20 and 10 cm. respectively, and a sufficient tensile strength to substantially prevent the elastic fibers from excessively stretching the epidermis overlaying impaired portions of the dermis while accommodating the expansion of the dermis through cell growth, the method comprising:

taping the adhesive side of the membrane over the area to be protected; and maintaining the membrane in place for about 75% to 90% of the time from about the twentieth week through the termination of the pregnancy.

9. The method of claim 8 further including the step of applying a nonsensitizing moisturizing material to said area prior to the step of securing the membrane.

10. The method of claim 9 wherein the material comprises a non-oily, quick-drying, emulsion-based lotion having moisturizing and emollient properties.

* * * * *